United States Patent [19]

Masaki et al.

[11] Patent Number: 4,981,950
[45] Date of Patent: Jan. 1, 1991

[54] VASOCONSTRICTOR PEPTIDE

[75] Inventors: Tomoh Masaki; Katsutoshi Goto; Sadao Kimura, all of Tsukuba; Youji Mitsui, Chiba; Yoshio Yazaki, Tokyo; Masashi Yanagisawa, Tsukuba; Hiroki Kurihara, Tokyo, all of Japan

[73] Assignees: Takeda Chemical Ind., Ltd.; Director-General of Agency of Industrial Science and Technology of Ministry of International Trade and Industry, Osaka, Japan

[21] Appl. No.: 249,429

[22] Filed: Sep. 26, 1988

[30] Foreign Application Priority Data

Oct. 9, 1987 [JP] Japan ................. 62-255381

[51] Int. Cl.$^5$ ............... A61K 37/02; C07K 7/10
[52] U.S. Cl. .................. 530/326; 435/70.3; 514/13
[58] Field of Search .......... 514/13; 530/326; 435/68, 70, 71

[56] References Cited

U.S. PATENT DOCUMENTS

| 4,496,544 | 1/1985 | Needleman | 514/13 |
| 4,557,864 | 12/1985 | Needleman | 530/326 |
| 4,618,600 | 10/1986 | Johnson et al. | 514/13 |
| 4,716,147 | 12/1987 | Tjoeng et al. | 530/326 |

OTHER PUBLICATIONS

Physiol., 248, C550, (1985), A. Kristine et al.
Am. J. and J. Cell. Physiol., 132, 263, (1987), (R. F. O'Brien et al.).
J. Pharmac. Exp. Ther., 236, 339, (1985), (M. N. Gillespie et al.).
I. Kifor and V. J. Dzav, Circ. Res., 60, 442, (1987).
M. Yanagawawa et al., Abstract, C-5, 77th Japan Pharmacological Meeting.
K. Takemoto, 79, 5485-5489, (1982).
C. Minth et al., Proc. Natl. Acad. Sci., (U.S.A.), 81, 4577-4581, (1984).
K. A. Hickey et al., Am. J. Physiol., 248:C550-C556, (1985).
R. F. O'Brien et al., J. Cell Physiol., 132, 263-270, (1987).
M. N. Gillespie et al., J. Pharmacology and Experimental Therapeutics, 236, 339-343, (1986).
K. Kifor and V. J. Dzau, Circulation Research, 60, 422-428, (1987).
M. Yanagisawa et al., Nature, 332, 411-415.
Y. Itoh et al., FEBS Letters, 231(2), 440-444, (1988).

Primary Examiner—Lester L. Lee
Attorney, Agent, or Firm—David G. Conlin; Peter F. Corless

[57] ABSTRACT

Disclosed is a vasoconstrictor peptide called Endothelin having a molecular weight of 2,500±300. Endothelin contains 21 amino acid residues, wherein four cysteines form two sets of S—S bond.

In order to obtain the vasoconstrictor factors of the present invention, it is preferable to culture the endothelial cells collected from the vascular inner walls in a serum-free medium.

The vasoconstrictor peptides of the present invention can be utilized as hypotension therapeutic agents or local vasoconstrictors to animals including humans.

3 Claims, No Drawings

VASOCONSTRICTOR PEPTIDE

BACKGROUND OF THE INVENTION

The present invention relates to a peptide having a vascular smooth muscle constrictor action. More particularly, the invention is directed to a new polypeptide or protein having a molecular weight of 2500±300, which has vasoconstrictor action, and which is preferably obtained from mammalian or bird endothelial cells, and to methods of making and using that polypeptide, as well as to pharmaceutical compositions employing such polypeptide.

There have been reported endothelium-dependent vasoconstrictor reactions to various mechanical and chemical stimuli as well as endothelium-dependent vasodilative reactions. For example, it is known that vasoconstrictions can be induced by a mechanical load such as vascular stretch or increased vascular inner pressure, or can be chemically induced by such agents as thrombin, noradrenaline, vasopressin, bradykinin, conditions of anoxia, etc. It has also been reported that noradrenaline-induced vasoconstriction can be enhanced by use of neuropeptide Y. [K. Takemoto, Proc. Natl. Acad. Sci. U.S.A. 79, 5485 (1982); C. Minth et al., ibid. 81, 4577 (1984)]. However, no endothelium-derived humoral factor mediating these constrictor reactions has yet been identified. Endothelial cell-derived coronary vascular constrictor factors (each having molecular weights of 8,500 and 3,000) are described in Physiol. 248, C550 (1985) A. K. Hickey et al., Am. J. and J. Cell. Physiol. 132, 263 (1987) (R. F. O'Brien et al.). However, their structures are unknown. An endothelial cell-derived peptide-like substance is also described in J. Pharmac. Exp. Ther. 236, 339 (1985) (M. N. Gillespie et al.). However, the structure of that substance is also unknown.

Certain peptides having a vasoconstrictor activity are known, such as vasopressin, bradykinin and the like, the amino acid sequences of which have been determined. It has *not* been reported, however, that such peptides were obtained from mammalian or bird vascular endothelial cells. Further, there is a report that angiotensin having a vasoconstrictor activity is obtained from the endothelial cells of bovine aortas [I. Kifor and V. J. Dzav, Circ. Res. 60, 422 (1987)]. However, angiotensin is a peptide having a molecular weight of about 1,000.

SUMMARY OF THE INVENTION

The present inventors have discovered a factor which has strong vascular smooth muscle constrictor activity which is produced from endothelial cells, e.g., from the endothelial cells of porcine aortas. This active factor is a novel peptide.

In accordance with the present invention, there is provided a peptide having a vascular smooth muscle constrictor activity for animals including humans which is obtained from mammalian or bird vascular endothelial cells and has a molecular weight of 2,500±300. The present inventors give a name "Endothelin" to it.

DESCRIPTION OF THE PREFERRED EMBODIMENTS

As the mammal, there can be mentioned human, monkey, horse, bovine, pig, dog, cat, rabbit, rat, mouse, guinea pig, hamster and the like. Sources of bird endothelial cells include chicken, duck, goose, turkey etc. Human, bovine, pig and rabbit endothelial cells are preferred. Usually, the mammalian and bird vascular endothelial cells can be easily obtained by methods which are known per se, e.g. rubbing vascular inner walls with a knife for anatomy or treating with an enzyme such as trypsin in the usual way. Aortas or umbilical veins are preferably used, because wider blood vessels are easy to be treated. The endothelial cells thus obtained show a strong vascular smooth muscle constrictor activity, when observed in the assay system which will hereinafter be described in a Reference Example. A cardiotonic action (a chronotropic action and an inotropic action to a heart) is also observed.

In order to obtain large quantities of the vasoconstrictor factor of the present invention, incubating of the endothelial cells obtained as described above is carried out. A serum culture or a serum-free culture may be used for the incubation. However, for the purpose of isolating the vascular smooth muscle constrictor factor of the present invention, the serum-free culture is highly preferable. Of the many suitable incubating procedures known monolayer subculturing is preferably employed. As a medium for the culture, the medium usually used for the culture of the higher animal cells, such as Ham F-10 medium is suitable. The medium is used in an amount of 0.05 to 5 ml, preferably 0.1 to 0.2 ml for $10^5$ endothelial cells. The culture term of the serum-free culture is preferably 0.5 to 8 days, most preferably 5 to 6 days. The culture temperature is usually 37°±1° C. The vascular smooth muscle constrictor action and the cardiotonic action are observed in the culture supernatant.

The vascular smooth muscle constrictor factor of the present invention was identified to be a peptide after its isolation and the purification.

For the isolation and the purification of the vascular smooth muscle constrictor peptide of present invention, there may be used known isolating and purifying methods for peptides, such as extraction, ion exchange or gel filtration chromatography, high performance liquid chromatography, electrophoresis and recrystallization. For the purpose of the present invention, ion exchange or reverse-phase chromatography or high performance liquid chromatography is particularly suitable.

Endothelin, the peptides according to the present invention, has 21 amino acid residues, including four cysteine groups located at 1st, 3rd, 11th and 15th from the N-terminus of the amino acid sequence, which form two sets of disulfide bonds. One of the combinations of the disulfide bonds may be 1-15 and 3-11 cysteines and the other combination may be 1-11 and 3-15. Activity of the former combination is higher than the latter one.

One of the isolated and purified peptides of the present invention is elucidated to be a peptide consisting of the following 21 amino acid residues (hereinafter referred to as compound I) from amino acid analysis (ninhydrin method), molecular weight measurement and other data;

Cys Ser Cys Ser Ser Leu Met Asp-Lys Glu Cys Val Tyr Phe Cys His Leu Asp Ile Ile Trp and has 2 sets of S—S bonds between Cys and Cys. The molecular weight thereof is 2,492.

The vasoconstrictor peptides of the present invention including compound I not only can be utilized as hypotension therapeutic agents or local vasoconstrictors but also give a clue to analysis of the mechanism of the vasoconstrictor reactions in vivo or to elucidation of the antagonists to the vasoconstrictor factors.

For example, the vasoconstrictor peptides of the present invention have such an effect as preventing various hemorrhage, for example, gastric or esophageal hemorrhage as vasoconstrictors. And the peptides have also an effect of curing various shock symptoms. The peptides can be administered orally, locally, intravenously or parenterally, preferably locally or intravenously. The dose is 0.001 $\mu$g–100 $\mu$g/kg, preferably 0.01 $\mu$g–10 $\mu$g/kg. The dose dependent on weight is in the form of a solution in 1–10 ml of isotonic sodium chloride solution.

The peptides of the present invention can be formed into various preparations, containing the peptide and additional components, such as emulsion, hydrated mixture, tablet, solution, powder, granules, capsule, pill etc. Said additional components include pharmaceutically acceptable vehicles, disintegrators, lubricants, binders, dispersants, plasticizers, fillers, carriers etc. As examples of the additional components, the examples of vehicles are lactose, glucose and white sugar; those of disintegrators are starch, sodium alginate, agar powder and carboxymethyl cellulose calcium; those of lubricants are magnesium stearate, talc and liquid paraffin; those of binders are syrup, gelatin solution, ethanol and polyvinyl alcohol; those of dispersants are methyl cellulose, ethyl cellulose and shellac; and those of plasticizers are glycerin and starch.

REFERENCE EXAMPLE (1) Assay of Vascular Smooth Muscle Constrictor Activity

Porcine right coronary artery spiral specimens ($2 \times 20$ mm) with the intima denuded by rubbing with a small swab are suspended in 3 ml of Krebs-Ringer solution maintained at 37° C. and saturated with the mixed gas containing 5% carbon dioxide and 95% oxygen by volume. After setting the basal tension to 1 g, the isometric tension is measured with tension transducers.

(2) Assay of Cardiotonic Action

Instead of the porcine right coronary artery spiral specimens used in the assay described in the above item (1), guinea pig right atrium suspended specimens are used, and the tension and the heart rate per minute are measured according to the same procedure as described in (1). (3) $ED_{50}$ Median effective dose. Effective dose for 50% of tested animals.

EXAMPLE 1

(1) Culture

Endothelial cells ($3.6 \times 10^4$) of porcine aortas subcultured through 10 to 20 cycles were grown to a confluent monolayer in 9.6 l of Dulbecco's modified Eagle's minimal essential medium containing 10% horse serum, at 37° C. in the atmosphere containing 5% carbon dioxide, on a plastic dish having a total culture area of 36,000 cm². It took 10 days. The cell density at this time was $10^5$/cm², namely the total cell number was $4.8 \times 10^9$. Subsequently, the medium was changed with 9.6 l of serum-free Dulbecco's modified Eagle's minimal essential medium, and the culture was continued at 37° C. for 5 days. The medium after the culture was centrifuged at 10,000 G for 20 minutes to remove suspended matter to obtain 9.6 l of a supernatant.

(2) Isolation and Purification of Compound I (i) Concentration and Desalting by Reverse-Phase Column The culture supernatant obtained in (1) was loaded onto a Chemcosorb SP-C-ODS reverse-phase column (3 cm in diameter $\times$ 18 cm in length, Chemco) equilibrated with a 0.1% trifluoroacetic acid solution (pH 2.0). The adsorbate was eluted with 30 ml of a 0.1% trifluoroacetic acid/70% acetonitrile solution (pH 2.0). After the eluate was extracted with 300 ml of diethyl ether, the organic phase was discarded and then 20 ml of the aqueous phase was adjusted to pH 7.0 by adding a 1M Tris base [Tris(hydroxymethyl) aminomethane] solution.

(ii) Crude Fractionation by Anion-Exchange Chromatography

The fraction (20 ml) obtained in (i) was loaded onto a Toyopearlpak DEAE-650M column (2.2 cm in diameter $\times$ 20 cm in length, manufactured by Tosoh) connected to a high performance liquid chromatography system and equilibrated with 20 mM Tris hydrochloric acid (pH 7.0), and a gradient of NaCl from 0.3M to 0.8M in 20 nM Tris hydrochloric acid (pH 7.0) was applied at a flow rate of 4 ml /min for 30 minutes. The vasoconstrictor activity of each fraction was assayed, and 40 ml of the fraction eluted with 0.5M NaCl was used as an active fraction.

(iii) Final Purification by Reverse-Phase High Performance Liquid Chromatography The active fraction (40 ml) obtained in (ii) was applied on a Unicil Q C18 column (7.5 mm in diameter $\times$ 30 cm in length, Gasukuro-Kogyo) equilibrated with a 0.1% trifluoroacetic acid solution. The adsorbed material was eluted with a gradient acetonitrile from 15% to 50% in a 0.1% trifluoroacetic acid solution at a flow rate of 3 ml/min for 70 minutes. The activity of each fraction was assayed, and 12 ml of the active fraction eluted with an acetonitrile concentration of 35% was obtained. This fraction was diluted three times with a 0.1% trifluoroacetic acid solution, then loaded on a Chemcosorb 5-ODS-H column (4.6 mm in diameter $\times$ 25 cm in length, Chemco) equilibrated with a 0.1% trifluoroacetic acid solution, and eluted with a gradient acetonitrile from 20% to 50% in a 0.1% trifluoroacetic acid solution at a column rate of 1 ml/min for 120 minutes. The eluate ultraviolet absorbance at 280 nm was monitored to fractionate the eluate by the peak of the absorbance. The active fraction was referred to as purified compound I, whose yield was 7.3 $\mu$g (2.9 n moles).

(3) Assay

The activity of the compound I obtained in 2 (iii) above was assayed by the method of Reference Example (1) and (2).

$ED_{50}$ by the assay (1) for smooth muscle constrictor activity to porcine coronary artery was 4 to $5 \times 10^{-10}$ mole/l.

$ED_{50}$ by the assay (2) for cardiotonic action to guinea pig right atrium was $1 \times 10^{-9}$ mole/l.

(4) Injection preparation

12 $\mu$g of compound I obtained in (2) is dissolved in isotonic sodium chloride solution for injection, then filtered by a Millipore filter, and lyophilized. An intravenous injection preparation is prepared, at use, by dissolving thus lyophilized product in isotonic sodium chloride solution for injection to a total volume of 5 ml.

EXAMPLE 2

Synthesis of Compound I (Endothelin)

Compound I was synthesized by the conventional method, using 0.7 g (0.5 m mole) of a commercial available protected tryptophan resin [Boc-Trp(CHO)-PAM resin, Applied Biosystems Inc., U.S.A.] and using a peptide synthesizer (Model 430A, Applied Biosystems Inc., U.S.A.).

Condensation process was conducted as follows:

The resin was treated with 50% trifluoroacetic acid in methylene chloride and a protected terminal amino group by Boc group was deprotected to free amino group. To the free amino group, the following protected amino acids were condensed in turn according to the amino acid sequence of Endothelin (Compound I) from the C-terminal in the presence of dicyclohexyl carbodiimide (DCC);

Boc-Ile, Boc-Asp(OBzl), Boc-Leu, Boc-His(Tos),
Boc-Cys(Acm), Boc-Tyr(Br-z), Boc-Val, Boc-Phe,
Boc-Glu(OBzl), Boc-Lys(Cl-Z), Boc-Met and Boc-Ser(Bzl).

800 mg of 1.8 g of the protected endothelin resin thus obtained was swelled with 1 ml of anithole and 1 ml of 1,2-ethanedithiole and then treated with 10 ml of hydrogen fluoride at 0° C. for 60 minutes followed by removal of excess hydrogen fluoride under reduced pressure. After washing the residue with 5 ml of ethyl acetate, it was extracted with 50% aqueous acetic acid and applied on a dextran gel column (Sephadex LH-20) (2×90 cm). Main active fractions eluted with the above solvent were collected to be lyophylized and then 120 mg of white powder was obtained. Twenty (20) mg of the powder was dissolved in 20 ml of 80% aqueous acetic acid and 15 mg of trifluoroacetate-mercury(II) was added thereto. After stirring at room temperature for 60 minutes, it was diluted with 30 ml of the above solvent and hydrogen sulfide gas was let therein and a deposit was filtered off and lyophilized. It was dissolved into 400 ml of dilute acetic acid and adjusted at pH 8 with ammonium hydrogen carbonate. After it was subjected to air-oxidation for 6 hours, acetic acid was added thereto to adjust it at pH 3 and it was lyophilized. It was applied on a Sephadex LH-20 column (2×90 cm) filled with 30% acetic acid and main fractions were collected. Further, it was fractionated by using HPLC (Column: YMC, Solvent: eluted by a linear gradient of 0.1% trifluoroacetic acid and acetonitrile containing 0.1% trifluoroacetic acid) and 2.7 mg of the desired product was obtained.

The synthesized endothelin (Compound I) was eluted by HPLC at the same position as that of the natural extracted endothelin:

Assay conditions (1)
  Column: Nucleosile 50 DS-H (Chemco) (4.61 mm $\phi \times 250$ mm)
  Eluent: A (0.1% aqueous trifluoroacetic acid), B (50% aqueous acetonitrile containing 0.1% trifluoroacetic acid).
  A linear gradient elution from the eluent A to the eluent B for 20 minutes.
  Flow rate: 1.0 ml/minute.

Assay conditions (2)
  Column: DEAE-2SW(Toyo Soda) (4.61 mm $\phi \times 250$ mm)
  Eluent: A (10 mM Tris.HCl pH 7.5), B (A containing 1M NaCl).
  A linear gradient elution from the eluent A to the eluent B for 40 minutes.
  Flow rate: 1.0 ml/minute.

Elution position: 21.5 minutes [assay conditions (1)], 21.3 minutes [assay conditions (2)].

We claim:

1. A vasoconstrictor peptide consisting essentially of the following amino acid sequence:

Cys Ser Cys Ser Ser Leu Met Asp Lys Glu Cys Val Tyr Phe
Cys His Leu Asp Ile Ile Trp

2. Vasoconstrictor peptide as claimed in claim 1, which is of vascular endothelial cells origin.

3. Vasoconstrictor peptide as claimed in claim 1, wherein four cysteines form two sets of S—S bonds.

* * * * *